US008268947B2

(12) United States Patent
Marchionni et al.

(10) Patent No.: US 8,268,947 B2
(45) Date of Patent: Sep. 18, 2012

(54) ADDITION REACTION TO FLUOROALLYLFLUOROSULFATE

(75) Inventors: Giuseppe Marchionni, Milan (IT); Vito Tortelli, Milan (IT)

(73) Assignee: Solvay Solexis S.p.A., Bollate (IT)

( * ) Notice: Subject to any disclaimer, the term of this patent is extended or adjusted under 35 U.S.C. 154(b) by 66 days.

(21) Appl. No.: 12/745,869

(22) PCT Filed: Dec. 17, 2008

(86) PCT No.: PCT/EP2008/067714
§ 371 (c)(1),
(2), (4) Date: Jun. 2, 2010

(87) PCT Pub. No.: WO2009/083451
PCT Pub. Date: Jul. 9, 2009

(65) Prior Publication Data
US 2010/0273968 A1 Oct. 28, 2010

(30) Foreign Application Priority Data

Dec. 28, 2007 (EP) .................................... 07025181

(51) Int. Cl.
C08F 16/24 (2006.01)
(52) U.S. Cl. ...................................................... 526/247
(58) Field of Classification Search ................... 526/247
See application file for complete search history.

(56) References Cited

U.S. PATENT DOCUMENTS

| 2,713,593 | A | 7/1955 | Brice et al. |
| 3,114,778 | A | 12/1963 | Fritz et al. |
| 4,235,804 | A | 11/1980 | Krespan |
| 4,273,728 | A | 6/1981 | Krespan |
| 4,275,225 | A | 6/1981 | Krespan |
| 4,292,449 | A | 9/1981 | Krespan |
| 4,962,282 | A | 10/1990 | Marraccini et al. |
| 7,009,018 | B2 * | 3/2006 | Oharu et al. .................. 526/247 |
| 2003/0153699 | A1 | 8/2003 | Ameduri et al. |
| 2005/0282986 | A1 | 12/2005 | Ameduri et al. |
| 2007/0293643 | A1 | 12/2007 | Ameduri et al. |

FOREIGN PATENT DOCUMENTS

| EP | 0460948 | A2 | 12/1991 |
| EP | 1574530 | A1 | 9/2005 |
| JP | 61276828 | A | 12/1986 |
| JP | 02138396 | A | 5/1990 |
| JP | 06275301 | A | 9/1994 |
| WO | WO 01/49760 | A1 | 7/2001 |

OTHER PUBLICATIONS

Wlassics et al. Molecules (2011), 16, 6512-6540.*
Krespan, C. G., et al. "Perfluoroallyl Fluorosulfate, a Reactive New Perfluoroallylating Agent", American Chemical Society, J. Am. Chem. Soc., 1981, vol. 103, p. 5598-5599, 2 pgs.
Banks R. E. et al., "Pefluoroallyl Fluorosulphonate", Elsevier Sequoia, Journal of Fluorine Chemistry, 1982, vol. 20, p. 1133-1134, 2 pgs.
Rozen S., "Selective Fluorinations by Reagents Containing the OF Group", American Chemical Society, Chem. Rev., 1996, vol. 96, p. 1717-1736, 20 pgs.
Navarrini W. et al,. "Organic perfluoro-hypofluorites : Useful reagents in the preparation of fluorinated vinylether monomers", Recent Res. Devel. Organic Chem., 2004, vol. 8, p. 281-322, 42 pgs.
Mukhametshin F.M., "Advances in the Chemistry of Organofluorine Hypohalites and Related Compounds", Russian Chemical Reviews, 1980, vol. 49, No. 7, p. 668-682, 15 pgs.
Hohorst F.A., "Bis(fluoroxy)difluoromethane, $CF_2(OF)_2$,", American Chemical Society, J. Am. Chem. Soc., 1967, vol. 89, p. 1809-1810, 2 pgs.
Vershilov S.V. et al., "Synthesis of 3-perfluoroalkyl-1,2,4-triazol-5-ylamines and -triazole-5-thiols", Russian Journal of Applied Chemistry, 1994, vol. 67(7), Part 2, p. 995-997, 3 pgs.

* cited by examiner

Primary Examiner — Nizal Chandrakumar
(74) Attorney, Agent, or Firm — Arent Fox LLP

(57) ABSTRACT

The invention pertains to a process for preparing compounds of formula (I-A) or (I-B) here below: by reaction of perfluoroallylfluorosulfate (FAFS) of formula (II): with at least one hypofluorite of formula (II-A) or (II-B): wherein: $R_F$ in formulae (I-A) and (II-A) is a monovalent fluorocarbon $C_1$-$C_{20}$ group, optionally comprising oxygen catenary atoms, optionally comprising functional groups comprising heteroatoms (e.g. —$SO_2F$ groups); $R'_F$ in formulae (I-B) and (II-B) is a divalent fluorocarbon $C_1$-$C_6$ group, preferably a group of formula

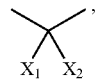

wherein $X_1$ and $X_2$, equal to or different from each other, are independently a fluorine atom or a $C_1$-$C_3$ fluorocarbon group. The FAFS-hypofluorite adducts of formulae (I-A) and (I-B) can be produced with high selectivity so as to access useful intermediates which can further be reacted taking advantage of the un-modified fluorosulfate group chemistry.

$R_FO$—$CF_2$—$CF_2$—$CF_2$—$OSO_2F$      (I-A)

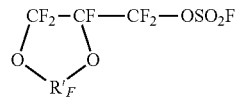

(I-B)

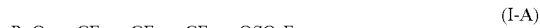

(II)

$R_FOF$      (II-A)

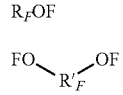

(II-B)

13 Claims, No Drawings

ADDITION REACTION TO FLUOROALLYLFLUOROSULFATE

CROSS-REFERENCE TO RELATED APPLICATIONS

This application is a U.S. national stage application under 35 U.S.C. §371 of International Application No. PCT/EP2008/067714 filed December 17, 2008, which claims priority to European Patent Application No.07025181.4 filed December 28, 2007, this whole content of this application being incorporated herein by reference for all purposes.

TECHNICAL FIELD

The present invention pertains to the addition reaction of hypofluorites to flouroallyfluorosulfate for yielding certain acy flouride derivatives, to synthetic methods comprising this addition reaction and to products obtainable therefrom.

BACKGROUND ART

Fluoroallylfluorosulfate (FAFS) is today an easily available fluorinated intermediate, which can be prepared in high yield notably via treatment of hexafluoropropylene with sulphur trioxide in the presence of boron-based catalysts, as disclosed in U.S. Pat. No. 4,235,804 (E.I. DUPONT DE NEMOURS) Nov. 25, 1980 and KRESPAN, G., et al. Perfluoroallylfluorosulfate, a reactive new perfluoroallylating agent. *J. Am. Chem. Soc.* 1981, vol. 103, p. 5598-5599.

This compound has been used with success in a large number of synthetic pathways wherein its reactivity towards nucleophilic agents and its ability to provide by appropriate nucleophilic substitution a perfluoroallyl group is exploited (see e.g. BANKS, Ronald E., et al. Perfluoroallyl fluorosulphonate. *Journal of Fluorine Chemistry.* 1982, vol. 20, p. 1133-1134).

Among others, mention can be made of synthetic processes involving the reaction of FAFS with polyfluorocarbonyl compounds in the presence of metal fluorides; these latter mentioned are in situ transformed in corresponding polyfluoroalkoxyde compounds which undergo nucleophilic substitution at the fluorosulfate group, yielding corresponding perfluoroallyl-substituted ether compound, as sketched in scheme here below:

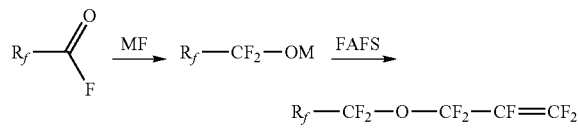

M = alkali metal or tetraaikylammonium
$R_f$ = fluorine-containing carbon group

Examples of such chemistry can be found in following documents: U.S. Pat. No. 4,292,449 (DU PONT) Sep. 29, 1981; U.S. Pat. No. 4,275,225 (DU PONT) Jun. 23, 1981; U.S. Pat. No. 4,273,728 (DU PONT) Jun. 16, 1981.

On the other side, no effort has been devoted to investigate the addition reactions of FAFS, in particular involving addition on its double bond of fluorine-containing compounds, e.g. hypofluorites, in particular for yielding fluorocarbonyl derivatives.

Actually, hypofluorites are well known to undergo addition reactions towards different olefins either via an electrophilic mechanism (ROZEN, S. *Chem. rev.* 1996, vol. 96, p. 1717 and ss.) or through a radical route (NAVARRINI, W., et al. Organic perfluoro-hypofluorites: useful reagents in the preparation of fluorinated vinylethers. *Recent Res. Devel. Organic Chem.* 2004, vol. 8, p. 281-322).

The Applicant has now surprisingly discovered that it is possible to add hypofluorites to the double bond of FAFS without incepting nucleophilic reactions on the fluorosulfate moiety. The FAFS is thus used as suitable synthone for the introduction in the target molecule of $C_3$-saturated oxygenated groups highlighted in scheme herein below:

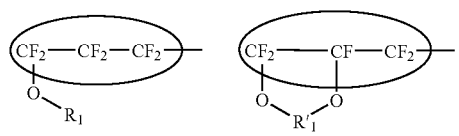

while preserving fluorosulfate moiety and accessible chemistry thereof, for providing corresponding acyl fluoride derivatives. Actually, reactivity of fluorosulfate groups in these intermediates can be used with success for the manufacture of fluoroacyl compounds, which are indeed interesting precursors for yielding different compounds, like, notably, fluoroethers which can undergo suitable dehydro/halogenation reactions for providing corresponding vinyl ethers.

DISCLOSURE OF INVENTION

It is thus an object of the present invention a process for preparing compounds of formula (III-A) and (III-B):

(III-A)

(III-B)

said process comprising:
(1) manufacturing compounds of formula (I-A) and (I-B):

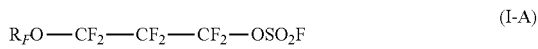

(I-A)

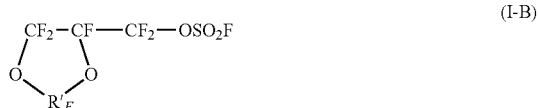

(I-B)

by reaction of perfluoroallylfluorosulfate (FAFS) of formula:

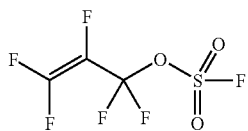

with at least one hypofluorite of formula (II-A) or (II-B):

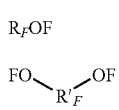

(2) converting compounds of formulae (I-A) and (I-B) as above detailed in corresponding acyl fluorides of formulae respectively (III-A) and (III-B) wherein:

$R_F$ in formulae (I-A), (II-A) and (IIIA) is a monovalent fluorocarbon $C_1$-$C_{20}$ group, optionally comprising oxygen catenary atoms, optionally comprising functional groups comprising heteroatoms (e.g. —$SO_2F$ groups);

$R'_F$ in formulae (I-B), (II-B) and (III-B) is a divalent fluorocarbon $C_1$-$C_6$ group, preferably a group of formula:

wherein $X_1$ and $X_2$, equal to or different from each other, are independently a fluorine atom or a $C_1$-$C_3$ fluorocarbon group.

The Applicant has surprisingly found that FAFS-hypofluorite adducts of formulae (I-A) and (I-B) can be produced with high selectivity so as to access useful intermediates which can further be reacted taking advantage of the un-modified fluorosulfate group chemistry for yielding the target carbonyl compounds comprising —COF groups.

Hypofluorites of formulae (II-A) and (II-B) and synthetic pathways towards these compounds are known in the art (see notably NAVARRINI, W., et al. Organic perfluoro-hypofluorites: useful reagents in the preparation of fluorinated vinylethers. *Recent Res. Devel. Organic Chem.* 2004, vol. 8, p. 281-322). Non-(imitative examples of hypofluorites of formula (II-A) are notably $CF_3OF$, $CF_3CF_2OF$, $CF_3CF_2CF_2OF$, $(CF_3)_2CFCF_2OF$, $CF_3OCF_2OF$, $CF_3OCF_2CF_2OF$, $CF_3CF_2OCF_2OF$, $CF_3CF_2OCF_2CF_2OF$, $CF_3CF_2CF_2OCF_2OF$, $CF_3OCF_2CF_2OCF_2OF$, $FSO_2CF_2CF_2OF$, $FC(O)CF_2OCF_2CF_2OF$. Non-(imitative examples of hypofluorites of formula (II-B) are notably $CF_2(OF)_2$, $CF(CF_3)(OF)_2$, $C(CF_3)_2(OF)_2$.

Reaction between FAFS and hypofluorites (II-A) and (II-B) is generally carried out at a temperature of from −150 to 0° C., preferably from −120° C. to −20° C. The skilled in the art will choose the appropriate temperature in view notably of the thermal stability of the hypofluorite involved.

Reaction pressure is generally atmospheric pressure, even if this is not a critical parameter.

Reaction is generally carried out in liquid phase, either in the absence or in the presence of an organic solvent inert in reaction conditions. Whereas no solvent is added, the FAFS itself advantageously provides for a liquid reaction medium. Non-(imitative examples of suitable organic solvents are notably chlorofluorocarbons, e.g. $CF_2Cl_2$, $CFCl_3$, $CF_2ClCFClCFClCF_2Cl$, perfluorocarbons, e.g. $CF_3CF_2CF_3$, perfluoroethers, e.g. $CF_3OCF_2CF_3$, chlorofluoroethers, e.g. $CF_3OCFClCClF_2$ or perfluoropolyethers, e.g. those of formula $CF_3O(CF_2CF_2O)_m(CF_2O)_nCF_3$, wherein m and n are integers such as their ratio is comprised between 0.1 and 5, and mixtures thereof.

Hypofluorites (II-A) and (II-B) are generally provided to the reaction medium diluted with an inert fluid either in gas or in liquid phase.

Typically, these diluting fluids are inert gas, like notably $N_2$, He, $CF_4$, $CF_3CF_3$ or $CF_3O$—$CF_2CF_3$.

Typically, a flow of hypofluorite (II-A) or (II-B) is fed into a reaction vessel comprising the FAFS; addition is generally continuously carried out during a prescribed time so as to fed the required amount of hypofluorite.

Target compounds (I-A) and (I-B) are then separated from the solvent (if any), from residual FAFS and recovered generally using fractional distillation techniques, either at standard pressure or under vacuum.

The Applicant thinks, without this limiting the scope of the invention, that the reaction between FAFS and hypofluorites (II-A) and (II-B) as above defined undergo a radical mechanism involving homolytic cleavage of O—F bond of the hypofluorite.

Adducts of formulae (I-A) and (I-B) can be widely used as intermediate in fluorine chemistry, in particular using peculiar reactivity of the fluorosulfate moiety.

The fluorosulfate moiety can notably undergo all well-known nucleophilic substitution reactions. Otherwise, FAFS adducts (I-A) and (I-B) as above described can be used for preparing corresponding acyl fluorides.

The process of the invention further comprises converting compounds of formulae (I-A) and (I-B) as above detailed in corresponding acyl fluorides of formulae respectively (III-A) and (III-B):

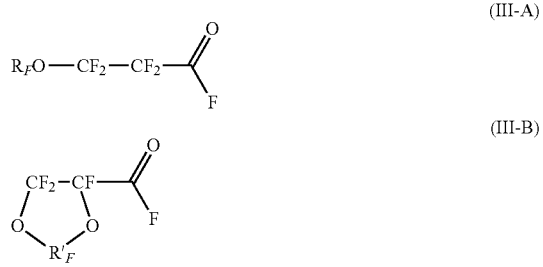

Standard methods for converting —$CF_2$—$OSO_2F$ moiety in —$C(O)F$ moiety can be used for transforming (I-A) and (I-B) in corresponding lower homologues acyl fluorides.

These methods can notably involve the hydrolysis, preferably the alkaline hydrolysis, of the FAFS adducts (I-A) and (I-B) as above defined and subsequent fluorination of the carboxylic moiety into the target acyl fluoride moiety.

Suitable reaction scheme can be sketched as follow:

Step 1

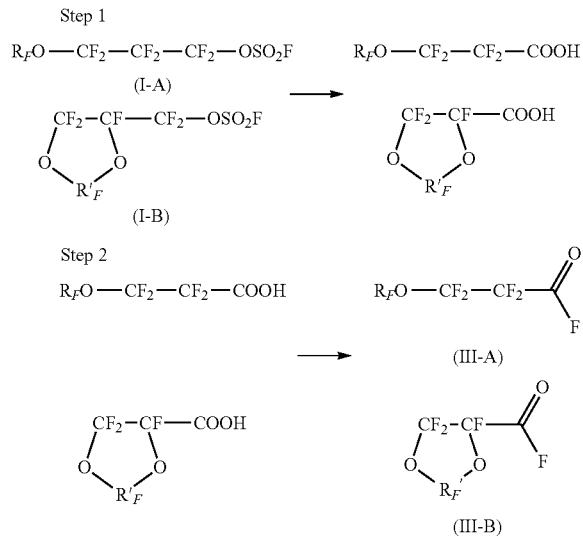

Step 2

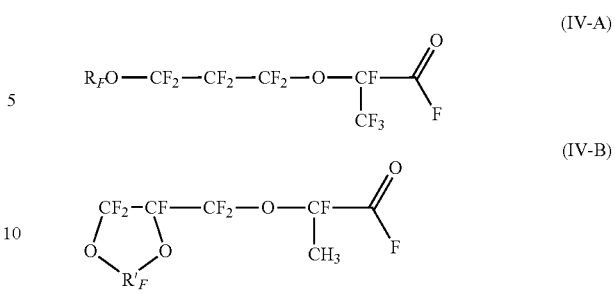

Hydrolysis (i.e. step 1 in Scheme) is preferably accomplished by alkaline hydrolysis with an aqueous inorganic base, e.g. with aqueous KOH, followed by treatment with an aqueous acidic solution (e.g. $HCl_{aq}$) for obtaining carboxylic acids.
Fluorination of the carboxylic moiety (i.e. step 2 in Scheme) can be performed:

- either by chlorination with $SO_2Cl$ (or other suitable chlorinating agent) and subsequent reaction of corresponding acyl chloride with KF (or other suitable fluoride source) to obtain the target acyl fluorides (III-A) and (III-B); or
- by treatment of carboxylic acid with a suitable fluorinating agent, like notably fluoroalkylamine reagents such as the Yarovenko's reagent ($Et_2N.CF_2CFClH$) or the Ishikawa's reagent ($Et_2N.CF_2CFHCF_3$) for directly yielding the target acyl fluorides (III-A) and (III-B).

Preferred method for converting (I-A) and (I-B) into acyl fluorides (III-A) and (III-B) involves the thermal decomposition of the —$CF_2$—$OSO_2F$ moiety in the presence of metal fluoride catalysts.

This method is particularly preferred because it enables obtaining the acyl fluorides (III-A) and (III-B) as above detailed in a one-step procedure, with high yields, generally exceeding 95%.

Preferred metal fluoride catalysts are CsF, KF, RbF, LiF, NaF, $CaF_2$, $BaF_2$, $MgF_2$, $SrF_2$, AgF. Most preferred metal fluorides are CsF and KF.

Reaction is generally carried out at a temperature between 20 and 200° C.

Chemistry of acyl fluorides (III-A) and (III-B) has been found to be particularly useful for the manufacture of ethers, particularly vinyl ethers.

According to a first variant of the invention, the process further comprises reacting the acyl fluorides (III-A) and (III-B) as above described with hexafluoropropylene epoxide (HFPO) in the presence of a suitable catalyst, so as to obtain compounds (IV-A) and (IV-B):

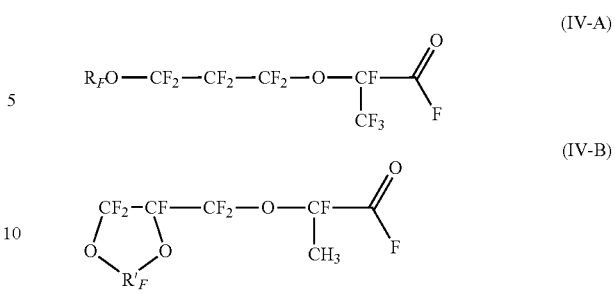

wherein $R_F$ and $R'_F$ have the meanings as above defined.

Reaction between acyl fluorides (III-A) and (III-B) with HFPO for yielding (IV-A) and (IV-B) can be carried out as described in U.S. Pat. No. 3,114,778 (DU PONT) Feb. 17, 1963.

The reaction can be carried out either in bulk using active carbon as catalyst or by reaction in a polar solvent using a fluoride catalyst, this latter embodiment being preferred. Fluoride catalysts suitable in the reaction are alkali metal fluorides, alkali-earth metal fluorides, quaternary ammonium fluorides and silver fluoride. Preferred fluoride catalysts are CsF, KF, RbF, LiF, NaF, $CaF_2$, $BaF_2$, $MgF_2$, $SrF_2$, AgF. Most preferred metal fluorides are CsF and KF.

Catalyst concentration is not critical and amounts of catalysts are determined by the environment in which the reaction is carried out. Reaction temperatures may be greatly varied from −80° C. to 200° C., although a preferred range is between −30° to 100° C.

The acyl fluorides (IV-A) and (IV-B) of the first variant of the invention may be further pyrolyzed to give the corresponding fluorovinyl ethers of formulae (V-A) and (V-B):

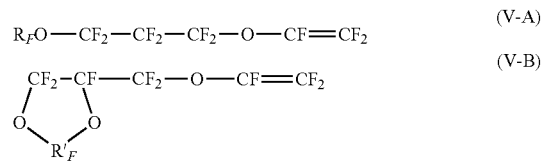

wherein $R_F$ and $R'_F$ have the meanings as above defined.

The pyrolysis can be carried out directly on the acyl fluorides (IV-A) and (IV-B) or these latter can be first converted into a monovalent metal salt, such as the alkali metal salt of the corresponding carboxylic acid and then pyrolyzed.

The hydrolysis and formation of the alkali metal salt is generally carried out by contacting the acyl fluorides (IV-A) and (IV-B) with water and then with alkali metal base such as KOH or NaOH. Pyrolysis of the alkali metal salt is generally carried out at a temperature of 150 to 250° C., preferably from 170° C. to 220° C.

The pyrolysis of the acyl fluorides (V-A) and (V-B) is generally effected in gas phase by contacting said acyl fluorides with a catalyst, preferably sodium sulfate or sodium carbonate, at a temperature of 150° to 350° C., preferably from 150° C. to 250° C.

According to a second variant of the invention, the process further comprises reacting in the liquid phase at temperatures from −150° C. to 0° C. the acyl fluorides (III-A) and (III-B) with elemental fluorine and at least one olefin compound [olefin (Ol)] of formula:

$$\begin{array}{c} A_1 \\ \diagdown \\ A_2 \end{array} = \begin{array}{c} A_3 \\ \diagup \\ A_4 \end{array}$$

wherein $A_1$, $A_2$, $A_3$, $A_4$, equal to or different from each other are chosen among H, F, Cl, Br, so as to obtain haloether compounds of formulae (VI-A) and (VI-B):

$$R_FO-CF_2-CF_2-CF_2-O-CA_1A_2-CFA_3A_4 \quad \text{(VI-A)}$$

$$\underset{R'_F}{\underset{O\diagdown \diagup O}{CF_2-CF}}-CF_2-O-CA_1A_2-CFA_3A_4 \quad \text{(VI-B)}$$

wherein $A_1$, $A_2$, $A_3$, $A_4$, $R_F$ and $R'_F$ have the meaning as above defined. It is generally preferred that olefin (Ol) to be used in this reaction step comprises at least one fluorine atom and at least one halogen atom chosen among bromine and chlorine. More preferred olefins (Ol) are those complying with formula here above wherein one of $A_1$ and $A_2$ is a fluorine atom, the remaining being chosen among H, Cl, Br, and wherein one of $A_3$ and $A_4$ is a fluorine atom, the remaining being chosen among H, Cl, Br. These preferred olefins (Ol) thus comply with formula:

$$CFA=CFA'$$

with A, A', equal to or different from each other, being independently selected among H, Cl, Br, preferably, A and A' being not simultaneously H.

Olefins (Ol) which are particularly suitable to the purposes of the invention are notably 1,2-dichloro-1,2-difluoroethylene (CFC 1112), 1,2-dibromo-1,2-difluoroethylene, 1-chloro-1,2-difluoroethylene. Most preferred olefin (Ol) is CFC 1112.

Haloethers compounds of formulae (VI-A) and (VI-B) according to this second variant of the preferred embodiment of the invention can be further reacted by dehalogenation/dehydrohalogenation for obtaining corresponding vinyl ethers (VII-A) and (VII-B):

$$R_FO-CF_2-CF_2-CF_2-O-CA_5=CFA_6 \quad \text{(VII-A)}$$

$$\underset{R'_F}{\underset{O\diagdown \diagup O}{CF_2-CF}}-CF_2-O-CA_5=CFA_6 \quad \text{(VII-B)}$$

wherein $A_5$ and $A_6$, equal to or different from each other, are chosen among H, F, Cl, Br, and $R_F$ and $R'_F$ have the meanings as above defined.

When the olefin (Ol) complies with formula $$CFA=CFA'$$

as above defined, fluorinated vinyl ethers of formulae (V-A) and (V-B), as above detailed, can be obtained.

Should $A_1$, $A_2$, $A_3$, $A_4$, equal to or different from each other, be chosen among F, Cl, Br, vinyl ethers can be obtained via a dehalogenation reaction. Dehalogenation can be accomplished by reaction of haloether compounds of formulae (VI-A) and (VI-B) in the presence of transition metals in polar organic solvents. Among suitable transition metals, mention can be made of Zn, Cu, Mn or mixtures Zn/Cu, Zn/Sn, Zn/Hg. Suitable polar organic solvents can be protic or aprotic. Among protic polar solvents, mention can be made of alcohols; among aprotic polar solvents, mention can be made of ethers (e.g. glyme, dioxane), dimethylformamide (DMF), dimethylsulfoxane (DMSO).

Should at least one of $A_1$, $A_2$, $A_3$, $A_4$ be hydrogen, vinyl ethers can be obtained via a dehydrohalogenation reaction.

Dehydrohalogenation can be accomplished by reaction of haloether compounds of formulae (VI-A) and (VI-B) in the presence of a base. Inorganic bases (e.g. NaOH or KOH) or organic bases (e.g. primary, secondary or tertiary alkyl or aryl amines) can be used. Generally, dehydrohalogenation is carried out in liquid phase, Optionally, in the presence of a solvent, typically aqueous or aqueous/alcoholic. When using aqueous inorganic bases, it is generally preferred to use a quaternary phosphonium or quaternary ammonium salts (e.g. tetrabutyl ammonium or phosphonium salts, especially chloride; trioctylbenzyl ammonium or phosphonium salts, especially chloride) or a sulfonium salt as phase transfer agent.

Both dehalogenation and dehydrohalogenation are typically carried out at a temperature from 0° C. to 150° C., preferably from 25° C. to 100° C.

According to a third variant of the invention, the process further comprises reacting the acyl fluorides (III-A) and (III-B) with elemental fluorine in the presence of a fluoride catalyst for obtaining the corresponding hypofluorites (VIII-A) and (VIII-B);

$$R_FO-CF_2-CF_2-CF_2OF \quad \text{(VIII-A)}$$

$$\underset{R'_F}{\underset{O\diagdown \diagup O}{CF_2-CF}}-CF_2OF \quad \text{(VIII-B)}$$

wherein $R_F$ and $R'_F$ have the meanings as above defined.

Fluoride catalysts suitable in the reaction are alkali metal fluorides, alkali-earth metal fluorides, quaternary ammonium fluorides and silver fluoride. Preferred fluoride catalysts are CsF, KF, RbF, LiF, NaF, $CaF_2$, $BaF_2$, $MgF_2$, $SrF_2$, AgF. More preferred metal fluorides are CsF and KF, most preferred is CsF.

Hypofluorites (VIII-A) and (VIII-B) can be widely used as useful intermediates in fluorine chemistry.

In particular, the process according to this variant can further comprises reacting the hypofluorites (VIII-A) and (VIII-B) with an olefin (Ol) as above defined for yielding corresponding haloether compounds of formulae (VI-A) and (VI-B), as above defined.

As mentioned for the second variant, haloether compounds (VI-A) and (VI-B) can be converted in corresponding vinyl ethers by dehalogenation/dehydrohalogenation, as above detailed.

All these synthetic schemes are based on the surprising reactivity of FAFS towards hypofluorites (II-A) and (II-B) as above described, which enable producing with high yields and selectivities fluorochemical synthons comprising fluorinated oxygen-containing groups of formulae:

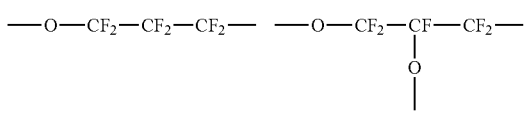

having —COF moieties susceptible of further reactivity.

Among compounds which can be manufactured from the methods above described, selected are new.

The invention thus also pertains to compounds of formula (IX-A) and (IX-B) here below:

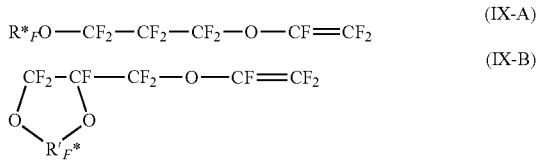

wherein $R^*_F$ is —$CF_2$—$CF_2$—$SO_2F$, —$C_2F_5$, —$(CF_2)_2$—$CF_3$, —$CF_2$—$COOCH_3$, and $R'^*_F$ is a —$CX^*_1X^*_2$-group, with $X^*_1$ and $X^*_2$, equal to or different from each other, being respectively —F or —$CF_3$.

Compound (IX-A) with $R^*_F$=—$CF_2$—$COOCH_3$ can be easily obtained from haloether compound (VI-A) with $R_F$=—$CF_2$—$CF_2$—$SO_2F$, by oxidation with $NO_2$, subsequent esterification with methanol of the so-obtained acyl fluoride, and final dehalogenation/dehydrohalogenation.

Compounds of formulae (IX-A) and (IX-B) can be used as monomers/comonomers for manufacturing corresponding polymers, optionally in combination with other (per)(halo)fluoromonomers.

In particular, compounds of formula (IX-A), wherein $R^*_F$ is —$CF_2$—$CF_2$—$SO_2F$, or —$CF_2$—$COOCH_3$ can be advantageously used for the manufacture of (per)fluorinated ionomers, suitable e.g. for production of membranes (e.g. for electrochemical cells or fuel cells).

Compounds of formula (IX-A), wherein $R^*_F$ is —$C_2F_5$, —$(CF_2)_2$—$CF_3$ can be advantageously used for the manufacture of (per)fluoroelastomers, e.g. in combination with vinylidene fluoride (VDF), tetrafluoroethylene (TFE) or mixture thereof.

Compounds of formula (IX-B) can be used for manufacturing thermoplastic (per)fluoropolymers, e.g. for the modification of TFE-based polymers.

The present invention will be now described in more detail with reference to the following examples whose purpose is merely illustrative and not intended to limit the scope of the invention.

Raw Materials

Perfluoroallylfluorosulphate (FAFS) has been synthesized accord to previously described techniques (KRESPAN, G., et al. Perfluoroallylfluorosulfate, a reactive new perfluoroallylating agent. *J. Am. Chem. Soc.* 1981, vol. 103, p. 5598-5599) and obtained with a selectivity of 80% (on converted $SO_3$) as a fluid having boiling point of 64° C.

Hypofluorites:

$CF_3OF$ was prepared as described in MUKHAMETSHIN, F. M. Advances in the Chemistry of Organofluorine Hypohalites and Related Compounds. *Russian Chemical Reviews.* 1980, vol. 49, no. 7, p. 668-682.

$CF_2(OF)_2$ was obtained as described in J. Am. Chem. Soc., 1967, vol. 89, p. 1809-1810;

$FSO_2$—$CF_2CF_2OF$ was prepared as described in U.S. Pat. No. 4,962,282 (AUSIMONT) Sep. 10, 1990.

EXAMPLE 1

Addition of $CF_3OF$ to FAFS and Synthesis of the $CF_3OCF_2CF_2CF_2OSO_2F$ Fluorosulphate Adduct.

A flow of 1.2 Nl/h of $CF_3OF$ diluted with 2.4 Nl/h of $N_2$, was fed during 2 hours through an inlet connection in a glass reactor having a capacity of 50 ml, equipped with a mechanical stirrer, containing 40 g of $CFCl_3$ and 16 g of FASF from Krespan et al., maintained at −50° C. with a cryogenic bath. At the end of the reaction, 56 g of a raw reaction mixture were obtained; FASF conversion was found to be 32% by GC/MS analysis. The fluorosulphate adduct of formula $CF_3OCF_2CF_2CF_2OSO_2F$ was obtained with a selectivity of 85.5% in moles (on converted FAFS). 10.2 g of unreacted FASF were recovered by fractional distillation.

EXAMPLE 2

Synthesis of the $CF_3OCF_2CF_2COF$ Acyl Fluoride

In a glass reactor having a capacity of 50 ml, equipped with a mechanical stirrer and connected, by means of a circulating-water cooling jacket, to a cold trap maintained at −70° C., were loaded 10 g of the fluorosulphate adduct prepared according to Example 1 and 0.1 g of CsF.

The mixture so obtained was heated through an external bath and refluxed for 2 hours, under vigorous stirring. At the end of the reaction, 6.8 g of $CF_3OCF_2CF_2COF$ acyl fluoride were recovered in the cold trap with a selectivity of 98% in moles, calculated on the moles of the fluorosulphate adduct, whose conversion was complete.

EXAMPLE 3

Synthesis of $CF_3O(CF_2)_3OCFClCF_2Cl$

A flow of 1.0 Nl/h of fluorine, diluted with 5.0 Nl/h of $N^2$, was fed during 6.5 hours in a glass reactor having a capacity of 50 ml, equipped with a mechanical stirrer, containing 57 g of CFCl=CFCl (CFC 1112) and 25.5 g of $CF_3O(CF_2)_2COF$ acyl fluoride from Example 3, and cooled at −100° C., (during the fluorine feeding period, a slight exothermic reaction was observed). The gaseous products collected at the exit of the reactor were allowed to pass through a trap maintained at −80° C. and containing a fluorinated solvent. At the end of the reaction, a raw reaction mixture was isolated from the reactor and from the trap which was characterized by GC/MS analysis: the conversions of CFC 1112 and of acyl fluoride were found to be respectively 100% and 60%. $CF_3O(CF_2)_3OCFClCF_2Cl$ was obtained with a selectivity of 75% in moles, calculated on the moles of the converted acyl fluoride.

EXAMPLE 4

Dehalogenation of $CF_3O(CF_2)_3OCFClCF_2Cl$

Powdered zinc (15 g), potassium carbonate (0.5 g), iodine (100 mg) and dimethylformamide (150 ml) were introduced into a three-neck round-bottom flask having an inner volume of 250 ml, equipped with a mechanical stirrer, a thermometer, a dropping funnel, a distillation column with a water cooling pipe and a collecting flask maintained at −78° C., connected to a vacuum line. The internal temperature was raised to 80°

C. and 57 g of $CF_3O(CF_2)_3OCFClCF_2Cl$ from Example 4 were added dropwise. At the end of the addition, the reaction mixture was allowed to react for about 30 minutes; the internal pressure was then gradually reduced from 760 mm Hg to 300 mm Hg. After 20 minutes, the internal pressure was restored to 760 mm Hg and the recovered collecting flask was found to contain 43 g of $CF_3O(CF_2)_3OCF=CF_2$ (b.p. 64° C.).

EXAMPLE 5

Addition of $FSO_2$—$CF_2CF_2OF$ to FASF and Synthesis of the $FSO_2$—$CF_2$—$CF_2$—$O$—$CF_2$—$CF_2$—$CF_2$—$OSO_2F$ Fluorosulphate Adduct (2A)

A flow of 0.8 Nl/h of $SO_2FCF_2CF_2OF$ hypofluorite, diluted with 17.6 Nl/h of helium was fed during 1 hour in a metallic reactor having a capacity of 50 ml, equipped with a mechanical stirrer, containing 18.3 g of $CF_2=CFCF_2OSO_2F$ (FAFS) and cooled at −50° C. At the end of the reaction, 24.1 g of a raw reaction product were obtained, from which, by means of a fractional distillation, 12 g of a 99% by weight fraction of a fluorosulphate adduct were recovered with a yield of 72% in moles, calculated on the moles of the $SO_2FCF_2CF_2OF$ hypofluorite, whose conversion was complete. The adduct of formula $SO_2$—$CF_2$—$CF_2$—$O$—$CF_2$—$CF_2$—$CF_2$—$O$—$SO_2F$ (2A) was characterized by means of GC/MS and $^{19}F$-NMR analysis.

EXAMPLE 6

Synthesis of the $FSO_2$—$CF_2$—$CF_2$—$O$—$CF_2$—$CF_2$—$COF$ Acyl Fluoride

Similar procedure as detailed in Example 2 was followed but the reactor, connected to a cold trap maintained at a temperature of 0° C., was loaded with 15 g of (2A) from Ex. 5. At the end of the reaction, the circulating-water cooling jacket was replaced by a Vigreux column and 11.4 g of $FSO_2$—$CF_2$—$CF_2$—$O$—$CF_2$—$CF_2$—$COF$ acyl fluoride were distilled off with a selectivity of 98% in moles, calculated on the moles of the fluorosulphate adduct, whose conversion was complete.

EXAMPLE 7

Synthesis of the $FSO_2$—$CF_2$—$CF_2$—$O$—$CF_2$—$CF_2$—$CF_2$—$O$—$CFCl$—$CF_2Cl$ Sulphonic Fluorohalogenether A flow of 1.6 Nl/h of fluorine, diluted with 8.0 Nl/h of $N_2$, was fed during 7 hours though an inlet connection in a glass reactor having a capacity of 50 ml, equipped with a mechanical stirrer, containing 59 g of CFC 1112 and 37 g of $FSO_2$—$CF_2$—$CF_2$—$O$—$CF_2$—$CF_2$—$COF$ acyl fluoride from Ex. 6, maintained at −80° C. At the end of the reaction, 110 g of a raw reaction product were recovered from the reactor and characterized by GC/MS analysis: the CFC 1112 conversion was 100% and that of the acyl fluoride was 58%. 24 g of $FSO_2$—$CF_2$—$CF_2$—$O$—$CF_2$—$CF_2$—$CF_2$—$OCFCl$—$CF_2Cl$ sulphonic fluorohalogenether were recovered from the raw reaction mixture by fractional distillation, the sulphonic fluorohalogenether obtained having a selectivity of 75% in moles, calculated on the moles of the converted acyl fluoride. 14.9 g of unreacted acyl fluoride were also recovered.

EXAMPLE 8

Dehalogenation of the $FSO_2$—$CF_2$—$CF_2$—$O$—$CF_2$—$CF_2$—$CF_2$—$OCFCl$—$CF_2Cl$ Sulphonic Fluorohalogenether Similar procedure as detailed in Ex. 4 was followed but using 8 g of powdered zinc and 70 ml of dimethylformamide and a collecting trap maintained at 0° C., connected to a vacuum line. The internal temperature was raised to 90° C. and 36 g of the fluorohalogenether prepared according to Example 8 were added dropwise. At the end of the addition, the mixture so obtained was allowed to react for about 30 minutes; internal pressure was gradually reduced from 760 mm Hg to 200 mm Hg. After 40 minutes, the internal pressure was restored to 760 mm Hg and the recovered collecting flask was found to contain 27 g of the sulphonic vinylether compound (yield 87%) having formula: $FSO_2$—$CF_2$—$CF_2$—$O$—$CF_2$—$CF_2$—$CF_2$—$OCF=CF_2$.

EXAMPLE 9

Synthesis of the fluorosulphate dioxolane having formula:

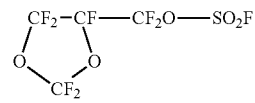

A flow of 1.0 Nl/h of $CF_2(OF)_2$ diluted with 2.0 Nl/h of $N^2$, was fed during 2 hours through an inlet connection in a glass reactor having a capacity of 50 ml, equipped with a mechanical stirrer, containing 20.5 g of FASF, maintained at −50° C. in a cryogenic bath. At the end of the reaction, 30 g of a raw reaction mixture were recovered; the FASF conversion was found by GC/MS analysis equal to 94%. 10.8 g of a pure dioxolane were recovered from the raw reaction mixture by fractional distillation, with a selectivity of 78% in moles, calculated on the moles of the fed bis-hypofluorite $CF_2(OF)_2$.

EXAMPLE 10

Synthesis of the acyl fluoride having formula:

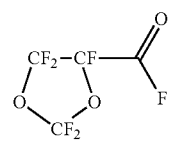

Similar procedure as detailed in Ex. 2 was followed but the reactor, connected to a cold trap maintained at a temperature of −78° C., was loaded with 9.4 g of the dioxolane prepared according to Example 9. The mixture so obtained was heated through an external bath and refluxed for 4 hours, under vigorous stirring.

At the end of the reaction, 6.2 g of the above-mentioned acyl fluoride were recovered in the cold trap with a selectivity of 98% in moles, calculated on the moles of the fluorosulphate dioxolane, whose conversion was complete.

EXAMPLE 11

Synthesis of the fluoroalogenether compound having formula:

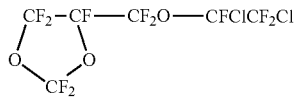

Similar procedure as detailed in Ex. 3 was followed but using 21 g of the acyl fluoride from Example 10, and an inlet flow of 1.6 Nl/h of fluorine, diluted with 8.0 Nl/h of $N_2$ for 7 hours. 17.6 g of the above-mentioned fluorohalogenether compound were recovered from the raw reaction mixture by fractional distillation, with a selectivity of 77% in moles, calculated on the moles of the converted acyl fluoride. 8.1 g of unreacted acyl fluoride were also recovered.

EXAMPLE 12

Dehalogenation of the fluorohalogenether compound of Ex. 11 and synthesis of a perfluorovinylether having formula:

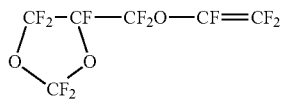

Similar procedure as detailed in Ex. 4 was followed but using 8 g of powdered zinc and 70 ml of dimethylformamide. The internal temperature was raised to 80° C. and 27 g of the fluorohalogenether compound of Example 11 were added dropwise. 21 g of the above-mentioned perfluorovinylether were recovered with a selectivity of 95% in moles, calculated on the moles of the converted fluorohalogenether.

The invention claimed is:

1. A process for preparing compounds of formula (III-A) and (III-B):

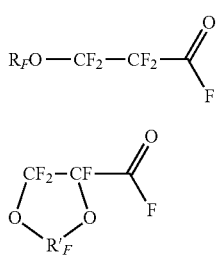

said process comprising:
(1) manufacturing compounds of formula (I-A) and (I-B):

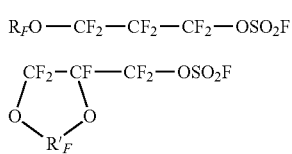

by reaction of perfluoroallylfluorosulfate (FAFS) of formula:

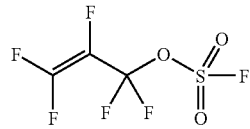

with at least one hypofluorite of formula (II-A) or (II-B):

(2) converting compounds of formulae (I-A) and (I-B) as above detailed to corresponding acyl fluorides of formulae respectively (III-A) and (III-B)
wherein:
$R_F$ in formulae (I-A), (II-A) and (IIIA) is a monovalent fluorocarbon $C_1$-$C_{20}$ group, optionally comprising oxygen catenary atoms, optionally comprising functional groups comprising heteroatoms; and
$R'_F$ in formulae (I-B), (II-B) and (III-B) is a divalent fluorocarbon $C_1$-$C_6$ group.

2. The process of claim 1, wherein said conversion in step (2) involves the thermal decomposition of the —$CF_2$—$OSO_2F$ moiety in the presence of metal fluoride catalysts.

3. The process of claim 2, wherein the metal fluoride is selected from the group consisting of CsF, KF, RbF, LiF, NaF, $CaF_2$, $BaF_2$, $MgF_2$, $SrF_2$, and AgF.

4. The process of claim 1, further comprising reacting the acyl fluorides (III-A) and (III-B) with hexafluoropropylene epoxide (HFPO) in the presence of a suitable catalyst, so as to obtain compounds (IV-A) and (IV-B):

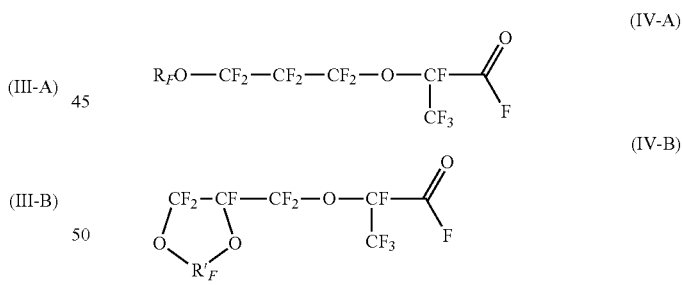

wherein $R_F$ and $R'_F$ have the meanings specified in claim 1.

5. The process of claim 4, further comprising pyrolyzing the acyl fluorides (IV-A) and (IV-B) to give the corresponding fluorovinyl ethers of formulae (V-A) and (V-B):

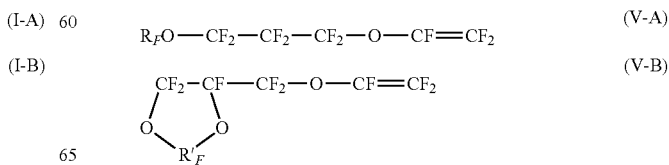

wherein $R_F$ and $R'_F$ have the meanings specified in claim 1.

6. The process of claim 5, wherein the pyrolysis of the acyl fluorides (V-A) and (V-B) is effected in gas phase by contacting said acyl fluorides with a catalyst at a temperature of 150° to 350° C.

7. The process of claim 1, further comprising reacting in the liquid phase at temperatures from −150° C. to 0° C. the acyl fluorides (III-A) and (III-B) with elemental fluorine and at least one olefin compound [olefin (Ol)] of formula:

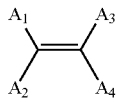

wherein $A_1$, $A_2$, $A_3$, $A_4$, equal to or different from each other are selected from the group consisting of H, F, Cl, and Br, so as to obtain haloether compounds of formulae (VI-A) and (VI-B):

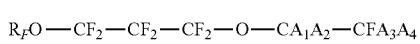 (VI-A)

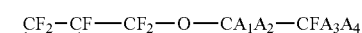 (VI-B)

wherein $A_1$, $A_2$, $A_3$, $A_4$ are as above, and $R_F$ and $R'_F$ have the meanings defined in claim 1.

8. The process of claim 7, wherein the olefin (Ol) is selected from the group consisting of 1,2-dichloro-1,2-difluoroethylene (CFC 1112), 1,2-dibromo-1,2-difluoroethylene, and 1-chloro-1,2-difluoroethylene.

9. The process of claim 7, wherein the haloethers compounds of formulae (VI-A) and (VI-B) are further reacted by dehalogenation/dehydrohalogenation for obtaining corresponding vinyl ethers (VII-A) and (VII-B):

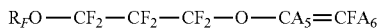 (VII-A)

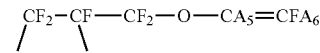 (VII-B)

wherein $A_5$ and $A_6$, equal to or different from each other, are chosen among H, F, Cl, Br, and $R_F$ and $R'_F$ have the meanings specified in claim 1.

10. The process of claim 1, further comprising reacting the acyl fluorides (III-A) and (III-B) with elemental fluorine in the presence of a fluoride catalyst for obtaining the corresponding hypofluorites (VIII-A) and (VIII-B);

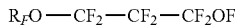 (VIII-A)

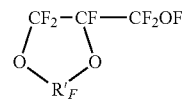 (VIII-B)

wherein $R_F$ and $R'_F$ have the meanings specified in claim 1.

11. The process of claim 10, said process further comprising reacting the hypofluorites (VIII-A) and (VIII-B) with one olefin compound [olefin (Ol)] of formula:

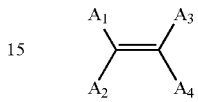

wherein $A_1$, $A_2$, $A_3$, $A_4$, equal to or different from each other are selected from the group consisting of H, F, Cl, and Br, yielding corresponding haloether compounds of formulae (VI-A) and (VI-B):

 (VI-A)

 (VI-B)
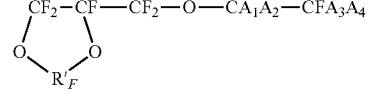

wherein $A_1$, $A_2$, $A_3$, $A_4$ are as above, and $R_F$ and $R'_F$ have the meanings defined in claim 1.

12. The process of claim 1, wherein $R'_F$ in formulae (I-B), (II-B) and (III-B) is a group of formula:

wherein $X_1$ and $X_2$, equal to or different from each other, are independently a fluorine atom or a $C_1$-$C_3$ fluorocarbon group.

13. The process of claim 1,
wherein the conversion in step (2) involves hydrolysis of compounds of formula (I-A) and (I-B) to obtain corresponding carboxylic compounds and subsequent fluorination of the carboxylic moiety to obtain the acyl fluorides of formula (III-A) and (III-B),
wherein the carboxylic compounds corresponding to compounds of formula (I-A) and (I-B) are

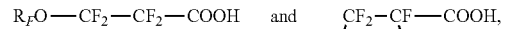 and 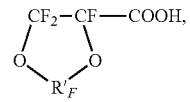

respectively, and
wherein $R_F$ and $R'_F$ have the meanings specified in claim 1.

\* \* \* \* \*